(12) United States Patent
Mandry

(10) Patent No.: US 12,575,793 B2
(45) Date of Patent: Mar. 17, 2026

(54) SELF-LEARNING INPUT FILTER FOR MEDICAL DEVICES

(71) Applicant: B. Braun Avitum AG, Melsungen (DE)

(72) Inventor: Peter Mandry, Dresden (DE)

(73) Assignee: B. Braun Avitum AG, Melsungen (DE)

( * ) Notice: Subject to any disclaimer, the term of this patent is extended or adjusted under 35 U.S.C. 154(b) by 1198 days.

(21) Appl. No.: 17/271,652

(22) PCT Filed: Aug. 29, 2019

(86) PCT No.: PCT/EP2019/073138
§ 371 (c)(1),
(2) Date: Feb. 26, 2021

(87) PCT Pub. No.: WO2020/043848
PCT Pub. Date: Mar. 5, 2020

(65) Prior Publication Data
US 2021/0338169 A1 Nov. 4, 2021

(30) Foreign Application Priority Data

Aug. 31, 2018 (DE) ..................... 10 2018 121 349.2

(51) Int. Cl.
*A61B 5/00* (2006.01)
*G06F 11/00* (2006.01)
(Continued)

(52) U.S. Cl.
CPC .......... *A61B 5/7221* (2013.01); *A61B 5/7225* (2013.01); *G06F 11/008* (2013.01);
(Continued)

(58) Field of Classification Search
None
See application file for complete search history.

(56) References Cited

U.S. PATENT DOCUMENTS 7,979,363 B1 7/2011 Minter
9,704,382 B2 7/2017 Kwon et al.
(Continued)

FOREIGN PATENT DOCUMENTS

CN 101718634 A 6/2010
CN 104965996 A 10/2015
(Continued)

OTHER PUBLICATIONS

Borowski, M., Siebig, S., Wrede, C. and Imhoff, M., 2011. Reducing false alarms of intensive care online-monitoring systems: an evaluation of two signal extraction algorithms. Computational and mathematical methods in medicine, 2011. (Year: 2011).*
(Continued)

*Primary Examiner* — G. Steven Vanni
*Assistant Examiner* — Meredith Abbott Vassell
(74) *Attorney, Agent, or Firm* — CM Law; Christopher A. Rothe

(57) ABSTRACT

A method for monitoring the reliability of an input in a medical device in which at least one value is entered into the medical device, an occurrence probability density of the at least one value is calculated on the basis of an input history, an error probability of the input is calculated from an a priori error probability density stored in a first database and loaded from the first database and the calculated occurrence probability density, and the error probability is output for further handling of the input.

8 Claims, 2 Drawing Sheets

(51) Int. Cl.

| | |
|---|---|
| *G06F 16/23* | (2019.01) |
| *G06N 7/01* | (2023.01) |
| *G16H 40/40* | (2018.01) |
| *G16H 40/63* | (2018.01) |

(52) U.S. Cl.
CPC .......... *G06F 16/2365* (2019.01); *G06N 7/01* (2023.01); *G16H 40/40* (2018.01); *G16H 40/63* (2018.01)

(56) References Cited

U.S. PATENT DOCUMENTS

| | | |
|---|---|---|
| 2007/0070038 A1 | 3/2007 | Hoffberg et al. |
| 2009/0043355 A1 | 2/2009 | Cazares et al. |
| 2015/0142457 A1 | 5/2015 | Marshall |
| 2017/0046499 A1 | 2/2017 | Hu et al. |
| 2017/0160112 A1 | 6/2017 | Guilley et al. |
| 2018/0242918 A1 | 8/2018 | Kogure et al. |

FOREIGN PATENT DOCUMENTS

| | | |
|---|---|---|
| CN | 106407082 A | 2/2017 |
| CN | 106529683 A | 3/2017 |
| CN | 106716072 A | 5/2017 |
| CN | 107137093 A | 9/2017 |
| CN | 107246873 A | 10/2017 |
| JP | 2000163404 A | 6/2000 |
| JP | 2015103243 A | 6/2015 |
| JP | 2015174256 A | 10/2015 |
| JP | 201747104 A | 3/2017 |
| RU | 2009108882 A | 9/2010 |

OTHER PUBLICATIONS

Thrun, S., 2002. Probabilistic robotics. Communications of the ACM, 45(3), pp. 52-57. (Year: 2002).*
Machine translation of Xiao et al., (CN106407082A, Feb. 15, 2017) (Year: 2017).*
Edworthy, "Medical audible alarms: a review," Edworthy J.J. Am Med Inform Assoc 2013, pp. 584-589, Oct. 25, 2012, 3 pages.
German Search Report received in Application No. 10 2018 121 349.2 dated Aug. 2, 2019, 20 pages.
Imhoff, et al., "Alarm Algorithms in Critical Care Monitoring," Anesth Anag [no date] 2006, pp. 1525-1537.
International Search Report received in Application No. PCT/EP2019/073138 dated Dec. 16, 2019, 5 pages.
Written Opinion received in Application No. PCT/EP2019/073138 dated Dec. 16, 2019, 12 pages.
Office Action received in Japanese Application No. 2021-510923 dated Oct. 17, 2023, with translation, 7 pages.
Office Action received in Chinese Application No. 201980061999.1 dated Dec. 26, 2023, with translation, 22 pages.
Office Action received in European Application No. 19 761 856.4-1122 dated Jul. 2, 2024, with translation, 14 pages.

* cited by examiner

SELF-LEARNING INPUT FILTER FOR MEDICAL DEVICES

CROSS-REFERENCE TO RELATED APPLICATION(S)

This application is the United States national phase entry of International Application No. PCT/EP2019/073138, filed Aug. 29, 2019, and claims the benefit of priority of German Application No. 10 2018 121 349.2, filed Aug. 31, 2018. The contents of International Application No. PCT/EP2019/073138 and German Application No. 10 2018 121 349.2 are incorporated by reference herein in their entireties.

FIELD

The present invention relates to a method for monitoring the reliability of an input to a medical device and to the field of medical devices, in particular to a device for monitoring the reliability of an input to a medical device.

BACKGROUND

Intensive care unit staff hear a variety of alarms during their daily work. There are between 150 and 350 alarms per patient per day, whereby different devices often compete for attention with almost indistinguishable sounds. As technization increases and patient monitoring becomes more invasive, the number of alarms and false alarms in intensive care units increases. Among other things, this can lead to desensitization and thus to endangering patients.

In this context, for example, the American Joint Commission on Accreditation of Healthcare Organizations, which is inter alia responsible for the certification of American hospitals, warns that alarm fatigue or alarm exhaustion/alarm weariness among employees endangers patient safety. In this regard, the Emergency Care Research Institute has stated this alarm fatigue as the greatest medical technology hazard for the past two years.

Alarm fatigue is desensitization, in particular of clinical staff, due to too many irrelevant alarms of medical devices. In addition to desensitization and overwork, which can cause inappropriate responses to alarms, too many alarms interrupt nursing activities, causing errors, and increase stress for patients. Furthermore, frequent and especially irrelevant alarms cause an unnecessary workload.

Causes for irrelevant alarms are, for example, the main preparation or measures on the patient, lack of adaptation of alarm thresholds to the patient or to the clinic situation, use of sensors with insufficient quality and service life, inadequate threshold logic, 'overmonitoring', proactive monitoring and/or faulty alarm transmission.

Most alarms sound due to predefined alarm thresholds being exceeded or undercut. These alarm thresholds are either hard-coded in the software or stored in a database that can be changed manually only with great effort. Thus, it is not possible for clinic staff to adjust alarm thresholds independently and in an easy way as needed.

The disadvantage of rigid programming of error thresholds is that these thresholds may not be appropriate for every situation. For example, aspirin can be used in the smallest doses to prevent platelet aggregation and in high doses to reduce pain. Thus, underdosing would not be detected by the database.

An algorithm for medical devices, as previously used with fixedly programmed alarm thresholds, is described in FIG. 3 of the figures below. Here, in step S1, at least one value is entered into the medical device. In step S9, the at least one value is calculated/compared with data from the database 1 (DERS database, which has already been adopted by known system). If the result in step S9 is positive (yes), the system goes to step S12 and outputs that the value is 'OK'. If the result in step S9 is negative (no), the system goes to step S11 and outputs an error message. Such an error message is followed by step S14, in which the operator is asked whether the value entered in step S1 should be overwritten. If the operator decides in step S13 against a new input, i.e. against overwriting the previous value, the algorithm is stopped. If the operator makes a new input in step S13, the previous value, which was evaluated as incorrect, is overwritten and then output as 'OK'. After that, the algorithm is finished/stopped until a new input is made (step S15).

Thus, the previous solutions have the disadvantage that the rigid definition of alarm thresholds when checking the correctness of the entered values leads to false alarms as well as unrecognized operating errors, which ultimately endangers the patient and in the worst case can lead to his or her death.

It is the object of the present invention to prevent the aforementioned disadvantages and problems and to provide a method and device to reduce false alarms, thereby increasing the safety of medical devices.

This object is solved by a method for monitoring the reliability of an input in a medical device and by a device for monitoring the reliability of an input in a medical device.

The present invention relates to a method for monitoring the reliability of an input to a medical device. In a first step, at least one value is entered into the medical device. After the input, an occurrence probability density of the at least one value is calculated based on an input history. The input history provides historical data, which is stored in a first database. Subsequently, in a further step, an error probability of the input is calculated from an a priori error probability density and the previously calculated occurrence probability density. The a priori error probability density is stored in the first database and is loaded from the database before the error probability is calculated. An a priori error probability density is a discrete or absolutely continuous density function with the associated probability distribution, i.e. the a priori probability distribution. After the error probability of the input has been calculated, it is output to the input handling for further use, such as for dynamically and independently adjusting alarm thresholds when checking the correctness of the at least one input value. In other words, this means that the alarm thresholds are adjusted based on the outputted error probability. Here, it is preferred if the adjustment of the alarm thresholds is performed independently/automatically.

With this method, the number of error messages can be reduced, in particular to the most important error messages, making it possible to reduce the risk of alarm fatigue. Furthermore, fewer misapplications have the advantage of reducing the number of victims of misapplications. In addition, the described flexible and self-learning method/system can reduce the workload of the clinic staff as well as the stress of the patients. In other words, inputs are evaluated and further processed with the help of a self-learning, flexible and adapting system—by means of artificial intelligence. Thus, the present invention provides a method that dynamically and autonomously adapts alarm thresholds to situations depending on values and experiences.

In an additional step, it is advantageous to store the at least one entered value in the first database, as well as to recalculate the a priori error probability density and to store the recalculated a priori error probability density also in the first database.

It is preferred to use a probability distribution based on a recursive Bayes filter to calculate the error probability. In other words, all inputs are stored in the first database in the medical device. The numerical values entered are recorded with the related/correlated inputs, such as alarms, alarm acknowledgements, alarm descriptions, and alarm cancellations.

An (input) filter in the style of a Bayes filter, such as Kalman, particle filter, Hidden Markov Model and/or Dynamic Bayer Network, calculates the a priori probability distribution from these values. Each new input is offset against this probability. Based on the resulting a posteriori probability, the input is evaluated by the algorithm and the input is declared/found valid or an alarm is issued if the input is declared/found invalid.

The Bayes filter or Bayesian estimation method differs from other estimation methods in classical statistics in that it treats the parameters to be estimated as random variables. As a consequence, a probability distribution over the resulting parameter space has to be specified a priori. This makes it possible to include prior information, such as in this case already known results of different inputs up to the time of the new input. After the specification of the a priori distribution, values/data are used to move from the a priori distribution to the a posteriori distribution on which the estimates are finally based.

The preceding method offers the possibility of an algorithm with adapting alarm thresholds. All inputs are recorded in the first database and an a priori distribution density and occurrence probability density are calculated for the values, from which the preceding filter calculates a validity value of the input.

The filter works in the function of a recursive Bayes filter type. Here, the a posteriori filter density can be determined recursively by the Bayesian estimation theory. Based on Bayes theorem, the a posteriori filter density can be first expanded and then factorized to obtain a recursive determination equation:

$$p(x_k \mid Y_k) = \frac{p(Y_k \mid x_k)p(x_k)}{p(Y_k)}$$

$$= \frac{p(y_k, Y_{k-1} \mid x_k)p(x_k)}{p(Y_k, Y_{k-1})}$$

$$= \frac{p(y_k \mid Y_{k-1}, x_k)p(Y_{k-1} \mid x_k)p(x_k)}{p(y_k \mid Y_{k-1})p(Y_{k-1})}$$

$$= \frac{p(y_k \mid Y_{k-1}, x_k)p(x_k \mid Y_{k-1})p(Y_{k-1})p(x_k)}{p(y_k \mid Y_{k-1})p(Y_{k-1})p(x_k)}$$

$$= \frac{p(y_k \mid Y_{k-1}, x_k)p(x_k \mid Y_{k-1})}{p(y_k \mid Y_{k-1})}$$

$$= \frac{p(y_k \mid x_k)p(x_k \mid Y_{k-1})}{p(y_k \mid Y_{k-1})}$$

In the equation, the variables xk, yk describe a value at time k, the variables Xk, Yk describe a sequence of all values up to time k, and the variable p describes a probability.

The denominator of the equation is a normalization constant, so the integral over the distribution function gives 1. Thus, only the predication or a priori distribution density $p(x_k|Y_{k-1})$ and the occurrence probability distribution density $p(y_k|x_k)$ in the numerator of the equation have to be determined. The a priori distribution density is calculated from the historical input data. These are input data which have already been evaluated as correct or incorrect in the past. The occurrence probability distribution density results from the probability of occurrence of the respective individual input values. For both calculations, the data are available in the first database.

Thus, when using the Bayes-based filter, it is advantageous that the filter adapts to the input behavior of its operator and is flexible to his or her changing behavior. The filter can learn permanently and will thus continue to independently filter out new types of incorrect input.

In a further step, it is preferred to use a predetermined probability distribution to determine the occurrence probability, in particular a Gaussian distribution based on the data of a second database, provided that no input history is available or no input history is available in sufficient quantity. This is especially advantageous at the beginning, when the first database has no historical data yet. The second database contains data from the previous Dose Error Reduction System (DERS) according to FIG. 3.

Furthermore, in a further step, all entered values are stored and the occurrence probability density of all input values is calculated as well as the a priori error probability density based on all input values. This procedure contains a training method according to the 'train-everything principle' (TEFT) and due to the fact that all inputs are included in the database, it offers the great advantage that the filter adapts very quickly to the new inputs and habits. However, this fact is at the same time connected with the fact that with fast changing input behavior in the preceding way, a lot of data is generated very fast, which can have unintentional strong influence on the evaluation and may lead to errors.

In an alternative step, only the entered values that have been judged to be erroneous by an operator are stored and then the a priori error probability density is recalculated on the basis of the initial a priori error probability density and the values that have been judged to be erroneous. In this train-on-error (TOE) method, the learning process of the filter is only initiated if an error has been committed while evaluating the input. As long as the operator does not explicitly overwrite an error message, the filter works only on the basis of the a priori probabilities learned at the beginning. For this reason, a filter working with this method adapts only slowly to newly appearing SPAM/errors. However, in comparison to the TEFT principle, relatively little memory is consumed for the dataset in this way.

Furthermore, in an alternative step, the calculation of the occurrence probability density and the recalculation of the a priori error probability density is interrupted as soon as a predetermined amount of stored values has been stored in the database for the at least one entered value. This interruption is cancelled when an operator has judged an entered value to be erroneous. This training method, called 'train-until-mature method' (TUM), is a compromise between the two preceding methods TEFT and TOE. Here, data points reach a predetermined amount of stored data/values, i.e. a certain 'maturity level'. Thus, the filter is not trained with these data points until an error message is overwritten. Only then is this data point added to the database accordingly or respectively the existing number is increased by one.

In a further alternative step, the filter is trained with test data until a certain threshold value, preferably corresponding to a work profile of the operator, is reached when calculating the error probability. In other words, the filter is trained with the test data in this 'train-until-no-error principle' (TUNE) until it reaches a certain threshold value when evaluating the input and thus corresponds to the operator's work profile. However, the filter can also be trained during use with TUNE in the event of an error with this incorrectly evaluated message. The disadvantage here is, however, that with TUNE the time of the training with test data can become extremely long depending on the extent of these data and computing power.

Thus, four training options are available with which the system can be trained.

Furthermore, the invention relates to a device for monitoring the reliability of an input in a medical device, comprising means for inputting at least one value into the medical device, means for calculating an occurrence probability density of the at least one value based on an input history, means for calculating an error probability of the input from an a priori error probability density stored in a first database and loaded from the first database and the calculated occurrence probability density, and means for outputting the error probability for further use in input handling.

Furthermore, the device described above is adapted to perform all the steps described above.

BRIEF DESCRIPTION OF THE DRAWING FIGURES

The invention is explained in more detail hereinafter by means of preferred embodiments with reference to the accompanying drawings.

DETAILED DESCRIPTION

In the following, embodiments of the present disclosure are described on the basis of the associated figures. Identical or functionally equivalent features are provided with the same reference signs in the individual figures and are not described more than once for the sake of convenience.

Figure 1:
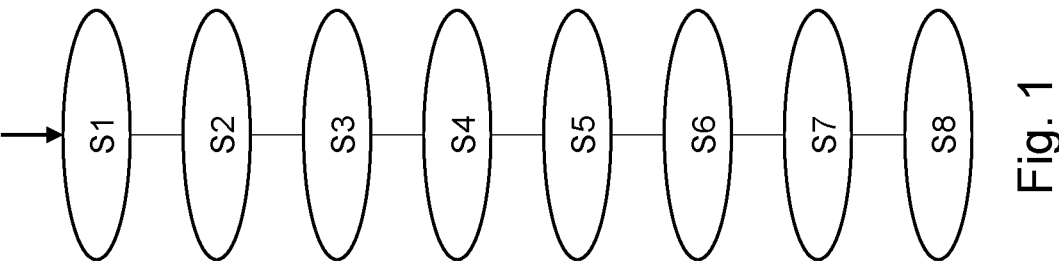
FIG. 1 shows a flowchart of a method for monitoring the reliability of an input.
Figure 3:
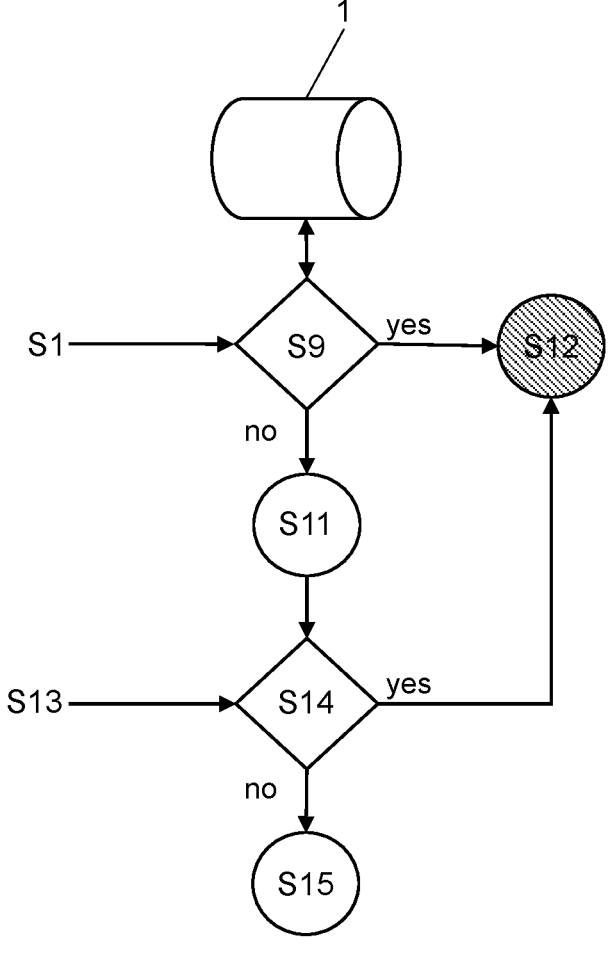
FIG. 3 shows an outlined algorithm with fixed alarm thresholds from the prior art.

FIG. 1 shows the sequence of the method for monitoring the reliability of an input in the form of a flow chart.

First, in step S1, the operator enters at least one value into the medical device, which is stored in a first database 3 in step S2. Then, in step S3, the occurrence probability density of the at least one value is calculated based on historical data. The historical data is stored in the first database 3. In a step S4, the a priori error probability density is loaded from the first database 3. From this loaded a priori error probability density and the occurrence probability density calculated in step S3, the error probability of the input is calculated in a calculation device 2 in step S5. In step S6, the error probability calculated in step S5 is output for further use in the input handling. In a final step S7, the a priori error probability density is recalculated and loaded into the first database 3 in step S8. In other words, a new data point is added to the first database 3.

Figure 2:
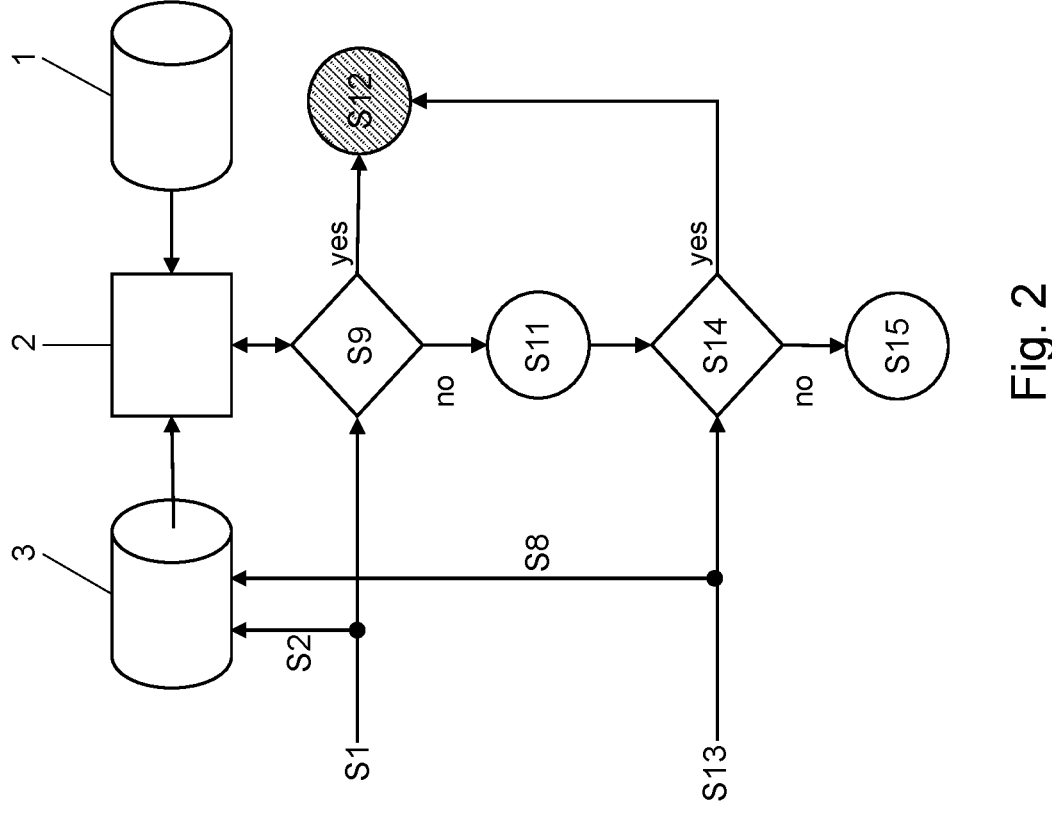
FIG. 2 shows an outlined algorithm with adapting alarm thresholds.

In FIG. 2, an algorithm with adapting alarm thresholds is outlined.

In a step S1, an operator enters at least one value into the medical device which is stored in the first database 3 in a step S2 and processed in the calculation device 2, which performs the algorithm, according to the flowchart in FIG. 1. The result output by the calculation device 2 or the output validity value of the input determines in step S9 whether the entered value is evaluated as positive/correct (yes) or negative/false (no).

In case the result output by the calculation device 2 is positive (yes), i.e. no alarm is output, the program goes to step S12. In step S12, it is output that the value is 'OK' and the algorithm is terminated.

In the case that the result output by the calculation device 2 is evaluated as negative (no), the next step S11 is performed, which outputs an error. In a further step S13, the operator has to decide whether to make a new input to overwrite the value in a step S14 or whether not to make a new input. In the first case, if the operator decides to overwrite the value in step S14, it is then proceeded to step S12 and again an 'OK' is output and the algorithm terminates. In the case where the operator decides not to make a new input and thus the value in step S14 is not overwritten, step S15 will be performed, which ends/stops the algorithm.

The invention claimed is:

1. A method for monitoring the reliability of input values into a medical device, comprising the steps of:

receiving an input value;

storing the input value;

storing historical input data as an input history;

storing predetermined probability distribution data and an a priori error probability density;

when an input history is available, calculating an occurrence probability density of the input value based on the input history, and when the input history is unavailable or an insufficient quantity of input history is available, using the predetermined probability distribution data to obtain the occurrence probability density;

calculating, using a recursive Bayes filter, an error probability of the input value from the a priori error probability density and from the calculated occurrence probability density, wherein outputs of the recursive Bayes filter adapt to changing input values;

using the calculated error probability to check correctness of the input value;

providing the input value to the medical device in accordance with correctness of the input value;

dynamically and independently adjusting an alarm threshold on the medical device based on the calculated error probability when checking correctness of the input value;

outputting an error when the input value has an erroneous value;

recalculating the a priori error probability density using the input value; and repeating the calculating the occurrence probability density, calculating the error probability of the input value, using the calculated error probability, providing the input value, adjusting the alarm threshold, outputting the error, and recalculating the a priori error probability density steps for a subsequent input value using the recalculated a priori error probability density.

2. The method according to claim 1, further comprising the step of:

calculating the error probability of the input value using at least one of a Kalman filter, a particle filter, a Hidden Markov Model, or a Dynamic Bayer Network.

3. The method according to claim 1, further comprising the steps of:

calculating the occurrence probability density of all input values and calculating the a priori error probability density based on all input values.

4. The method according to claim 1, further comprising the steps of:

storing the input value only when the input value has been judged to be erroneous by an operator, and recalculating the a priori error probability density based on an initial a priori error probability density and the input value judged to be erroneous.

5. The method according to claim 4, further comprising the steps of:

interrupting the calculation of the occurrence probability density and the recalculation of the a priori error probability density as soon as a predetermined amount of stored values has been stored for the input value; and suspending the interruption when an operator has judged the input value to be erroneous.

6. The method according to claim 1, further comprising the step of:

training with test data until a certain threshold value is reached in the calculation of the error probability.

7. The method according to claim 1, further comprising, after outputting the error when the input value has the incorrect value, enabling an operator of the device to provide a new input value to overwrite the input value.

8. A system for monitoring reliability of input values into a medical device, comprising:

a first database that stores an a priori error probability density, receives the input values, and stores historical input data as an input history;

a second database that stores predetermined probability distribution data; and a calculation device that calculates an occurrence probability density of an input value based on the input history when the input history is available and uses the predetermined probability distribution data when the input history is unavailable or an insufficient quantity of input history is available, the calculation device including a recursive Bayes filter that calculates an error probability of the input value from the a priori error probability density stored in the first database and loaded from the first database and from the calculated occurrence probability density to adapt outputs of the recursive Bayes filter to changing input values, wherein the calculation device further uses the calculated error probability to check correctness of the input value and provides the input value to the medical device in accordance with correctness of the input value, wherein the calculation device recalculates the a priori error probability density using the input value and stores the recalculated a priori error probability density for use by the recursive Bayes filter in determining the error probability of a subsequent input value, wherein the calculation device provides the input value to the medical device in accordance with correctness of the input value as determined from the calculated error probability, wherein an alarm threshold on the medical device is dynamically and independently adjusted by the calculation device based on the calculated error probability when checking correctness of the input value, wherein an error is outputted by the calculation device when the input value has an erroneous value, and wherein the calculation devices repeatedly calculates the occurrence probability density, calculates the error probability of the input value, uses the calculated error probability, provides the input value, adjusts the alarm threshold, outputs the error, and recalculates the a priori error probability density steps for subsequent input values using the recalculated a priori error probability density.

\* \* \* \* \*